(12) United States Patent
Machida et al.

(10) Patent No.: US 7,081,353 B2
(45) Date of Patent: Jul. 25, 2006

(54) DRUG SUSCEPTIBILITY MEASUREMENT METHOD AND APPARATUS THEREOF

(75) Inventors: Katsuhiko Machida, Tokyo (JP); Sadayori Hoshina, Tokyo (JP); Takashi Ushida, Ibaraki (JP); Junichiro Arai, Ibaraki (JP); Hideo Katayama, Ibaraki (JP); Chiaki Okumura, Ibaraki (JP); Yoshihisa Amano, Ibaraki (JP)

(73) Assignees: Jikei University School of Medicine, Tokyo (JP); Japan as Represented by Director-General of National Institute of Advanced Industrial Science and Technology, Ministry of Economy, Trade and Industry, Tokyo (JP); Daikin Industries, Ltd., Osaka (JP)

( * ) Notice: Subject to any disclaimer, the term of this patent is extended or adjusted under 35 U.S.C. 154(b) by 308 days.

(21) Appl. No.: 10/221,796

(22) PCT Filed: Mar. 20, 2001

(86) PCT No.: PCT/JP01/02199

§ 371 (c)(1),
(2), (4) Date: Jan. 2, 2003

(87) PCT Pub. No.: WO01/68906

PCT Pub. Date: Sep. 20, 2001

(65) Prior Publication Data

US 2003/0186351 A1 Oct. 2, 2003

(30) Foreign Application Priority Data

Mar. 17, 2000 (JP) .............................. 2000-081766

(51) Int. Cl.
C12M 1/34 (2006.01)
C12Q 1/18 (2006.01)

(52) U.S. Cl. ..................................... 435/32; 435/287.1

(58) Field of Classification Search .................. 435/25, 435/29, 32, 34, 40.5, 287.1; 436/800; 43/287.1
See application file for complete search history.

(56) References Cited

U.S. PATENT DOCUMENTS 4,209,586 A * 6/1980 Noller ........................ 435/32

FOREIGN PATENT DOCUMENTS

JP 2-222098 9/1990
JP 10-276795 10/1998

* cited by examiner

*Primary Examiner*—Jon Weber
*Assistant Examiner*—Kailash C. Srivastava
(74) *Attorney, Agent, or Firm*—Smith, Gambrell & Russell, LLP

(57) ABSTRACT

A method and apparatus wherein measurement current values output from a first oxygen sensor and a second oxygen sensor are time sequentially measured. Each moving average value is calculated from each sequential measurement current value. Each time differential value is calculated from the pair of each calculated moving average values, by least squares approximation. Then, drug susceptibility is measured based upon each calculated time differential value, so that drug the susceptibility measurement is performed quickly or accurately.

2 Claims, 3 Drawing Sheets

DRUG SUSCEPTIBILITY MEASUREMENT METHOD AND APPARATUS THEREOF

This application is a 371 of PCT/JP01/02199 filed 19 Mar. 2001 and claims priority to JP-2000-82766 filed 17 Mar. 2000.

TECHNICAL FIELD

This invention relates to a drug susceptibility measurement method and apparatus thereof. More particularly, the present invention relates to a method and apparatus to measure drug susceptibility by detecting a dissolved oxygen concentration within a first solution which includes measurement target bacteria and predetermined drug, and a dissolved oxygen concentration within a second solution which includes the measurement target bacteria and does not include the predetermined drug, with oxygen electrodes, respectively.

RELATED ART

A method for measuring drug susceptibility by detecting dissolved oxygen concentration with an oxygen electrode is known. Once such method involves preparing a first solution which includes measurement target bacteria and a predetermined drug, and a dissolved oxygen concentration within a second solution which includes the measurement target bacteria and does not include the predetermined drug. The method then detects dissolved oxygen amounts within both solutions as output signals (current values) using oxygen electrodes, respectively. The method collects (detection interval of 0.1 seconds)×5 data at every 2 seconds for 30 times. The method records average values, each being an average value of collected 60 data, as average data each for each time, respectively. The method carries out the following processing based upon the data per minute.

In the processing, it is supposed that a timely differential value of current value is employed instead of an absolute current value because an absolute current value may vary about 10–20% depending upon an oxygen electrode. An absolute current value is in proportion to a dissolved oxygen concentration, therefore a timely differential value of current value is in proportion to an oxygen consumption speed, that is a respiration amount of bacteria. A case in which the respiration amount (timely differential value) is decreased down to 50% of that of the second solution which does not include the drug and includes measurement target bacteria therein, is employed as a standard which represents a case in which respiration amount is suppressed. Further, a timing at which a current value becomes 0 for the second solution (oxygen within the second solution has missed) is employed as data used for analysis, and timely differential values of current values for the prior 10 minutes obtained by least-squares approximation are employed as data used for analysis, because a timing is desirable at which a difference in timely differential values appears to be a great value.

When this method is employed, drug susceptibility can be measured from both of the obtained timely differential values.

When the above method is employed, disadvantages arise in that a required time period for measuring drug susceptibility becomes a remarkably long time period, because measurement should be continued until a current value becomes 0.

It may be taken into consideration, to overcome such a disadvantage, that continuous analysis is carried out, for example, a timely differential value of each current value for 10 minutes and a ratio of a timely differential value for each drug concentration and a timely differential value for the second solution are used as data, and each variation is observed.

When such analysis is carried out with data which are obtained at every 1 minute, obtained timely differential value is greatly affected by noises of the data so that accurate analysis is difficult to be obtained. Further, when the ratio of the timely differential value and the timely differential value for the second solution are obtained, the ratio is more affected by noises of the second solution so that analysis accuracy is greatly lowered.

In many cases, the drug susceptibility measurement is carried out for the purpose of clinical inspection. In this case, it is strongly desired for curing a patient and thus rapid measurement and accurate measurement are tolerated.

The present invention was made in view of the above problems. It is an object of the present invention to offer a drug susceptibility measurement method and apparatus thereof which carry out measurement of drug susceptibility with short time period and accuracy.

DISCLOSURE OF THE INVENTION

A drug susceptibility measurement method according to the present invention concerns a method which measures drug susceptibility by detecting a dissolved oxygen concentration within a first solution which includes measurement target bacteria and a predetermined drug, and a dissolved oxygen concentration within a second solution which includes the measurement target bacteria and does not include the drug, with oxygen electrodes, respectively, the method comprises the steps of:

collecting output signals from the both oxygen electrodes at a second time interval for a first predetermined time period;

averaging each output signal from each oxygen electrode using prior and later predetermined number of output signals with respect to each output signal;

calculating each timely differential value of each moving averaged output signal; and measuring drug susceptibility using both timely differential values.

A drug susceptibility measurement apparatus according to the present invention is an apparatus which measures drug susceptibility by detecting a dissolved oxygen concentration within a first solution which includes measurement target bacteria and predetermined drug, and a dissolved oxygen concentration within a second solution which includes the measurement target bacteria and does not include the drug, with oxygen electrodes, respectively, the apparatus comprises:

collecting means for collecting output signals from both oxygen electrodes at a second time interval for a first predetermined time period;

averaging means for moving averaging each output signal collected from each oxygen electrode using prior and later predetermined number of output signals with respect to each output signal;

timely differential value calculating means for calculating each timely differential value of each moving averaged output signal; and drug susceptibility measuring means for measuring drug susceptibility using both calculated timely differential values.

When the drug susceptibility measurement method of the present invention is employed, and when the method measures drug susceptibility by detecting a dissolved oxygen concentration within a first solution which includes measurement target bacteria and predetermined drug, and a dissolved oxygen concentration within a second solution which includes the measurement target bacteria and does not include the drug, with oxygen electrodes, respectively, a drug susceptibility measurement is performed within a short time period and with accuracy.

The method collects output signals from both of the oxygen electrodes at a second time interval for a first predetermined time period. The method moving averages each output a signal from each oxygen electrode using a prior and later predetermined number of output signals with respect to each output signal. The method calculates each timely differential value of each moving averaged output signal. The method measures drug susceptibility using both of the timely differential values. Therefore, disturbance due to noises is reduced so that measurement accuracy is improved in comparison to a case in which a data row is created by simply averaging. Further, a required time period can be shortened because continuous analysis is carried out. As a result, improvement in measurement accuracy and shortening of the required time period can be done.

When the drug susceptibility measurement apparatus of the present invention is employed, and when the apparatus measures drug susceptibility by detecting a dissolved oxygen concentration within a first solution which includes measurement target bacteria and predetermined drug, and a dissolved oxygen concentration within a second solution which includes the measurement target bacteria and does not include the drug, with oxygen electrodes, respectively, a drug susceptibility measurement is performed within a short time period and with accuracy.

The apparatus collects output signals from both of the oxygen electrodes at a second time interval for a first predetermined time period using the collecting means. The apparatus moving averages each output signal collected from each oxygen electrode using prior and later predetermined number of output signals with respect to each output signal using the moving averaging means. The apparatus calculates each timely differential value of each moving averaged output signal using the timely differential value calculating means. The apparatus measures drug sensitivity using both of the calculated timely differential values using the drug susceptibility measuring means.

Therefore, disturbances due to noises is reduced so that measurement accuracy is improved in comparison to a case in which data row is created by simply averaging. Further, a required time period can be shortened because continuous analysis is carried out. As a result, improvement in measurement accuracy and shortening of required time period can be coped with.

BEST MODE FOR CARRYING OUT THE INVENTION

Hereinafter, referring to the attached drawings, a drug susceptibility measurement method and apparatus thereof according to the present invention is described in detail.

Figure 1:
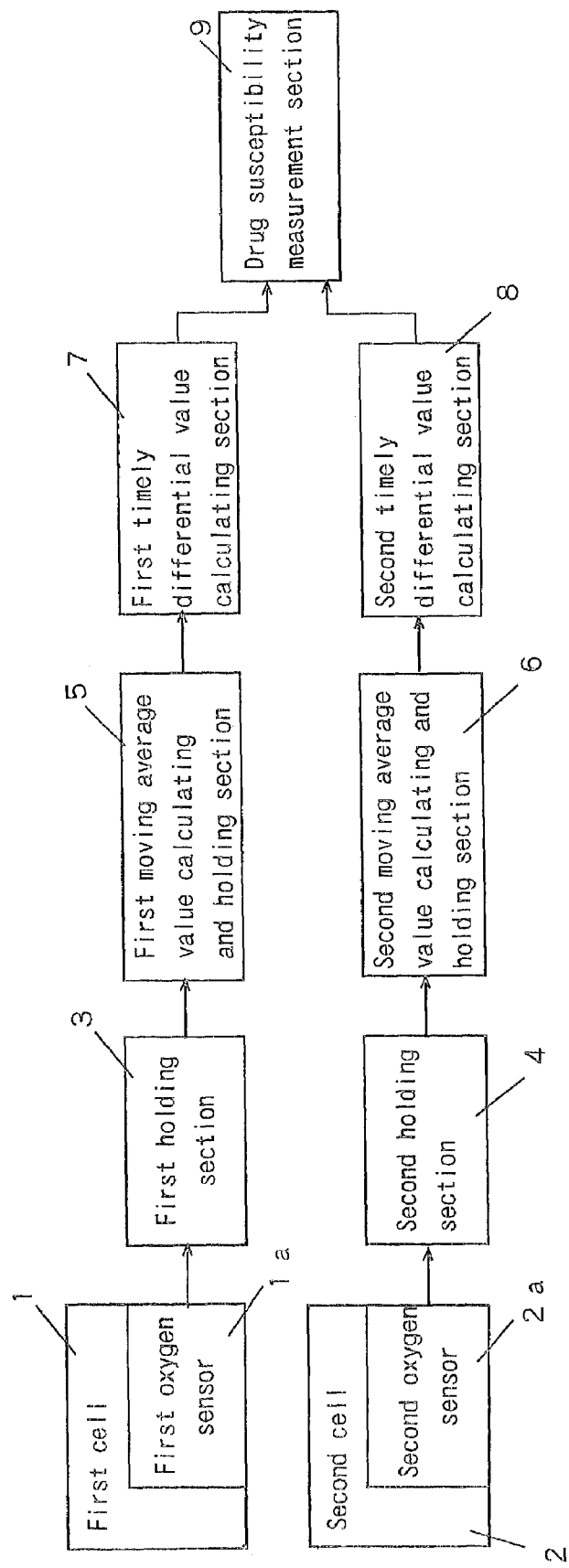
FIG. 1 is a block diagram illustrating a drug susceptibility measurement apparatus of an embodiment according to the present invention.

FIG. 1 is a block diagram illustrating a drug susceptibility measurement apparatus of an embodiment according to the present invention.

This drug susceptibility measurement apparatus comprises a first cell 1 for containing a first solution in which is added a drug and bacteria therein, a second cell 2 for containing a second solution in which the drug is not added but the bacteria is added therein, a first oxygen sensor 1a provided to the first cell 1, which detects dissolved oxygen concentration within the first solution and outputs a measurement current value therefrom, a second oxygen sensor 2a provided to the second cell 2, which detects dissolved oxygen concentration within the second solution and outputs a measurement current value therefrom, a first holding section 3 for holding the measurement current value output from the first oxygen sensor 1a, in a time sequential manner, a second holding section 4 for holding the measurement current value output from the second oxygen sensor 2a, in a time sequential manner, a first moving average value calculating and holding section 5 for calculating a moving average value from the measurement current values time sequentially held by the first holding section 3, and for holding the calculated moving average value in a time sequential manner, a second moving average value calculating and holding section 6 for calculating a moving average value from the measurement current values time sequentially held by the second holding section 4, and for holding the calculated moving average value in a time sequential manner, a first timely differential value calculating section 7 for calculating a first timely differential value from moving average values time sequentially held by the first moving average value calculating and holding section 5, a second timely differential value calculating section S for calculating a second timely differential value from moving average values time sequentially held by the second moving average value calculating and holding section 6, and a drug susceptibility measurement section 9 for measuring drug susceptibility based upon the first timely differential value and the second timely differential value.

Figure 2:
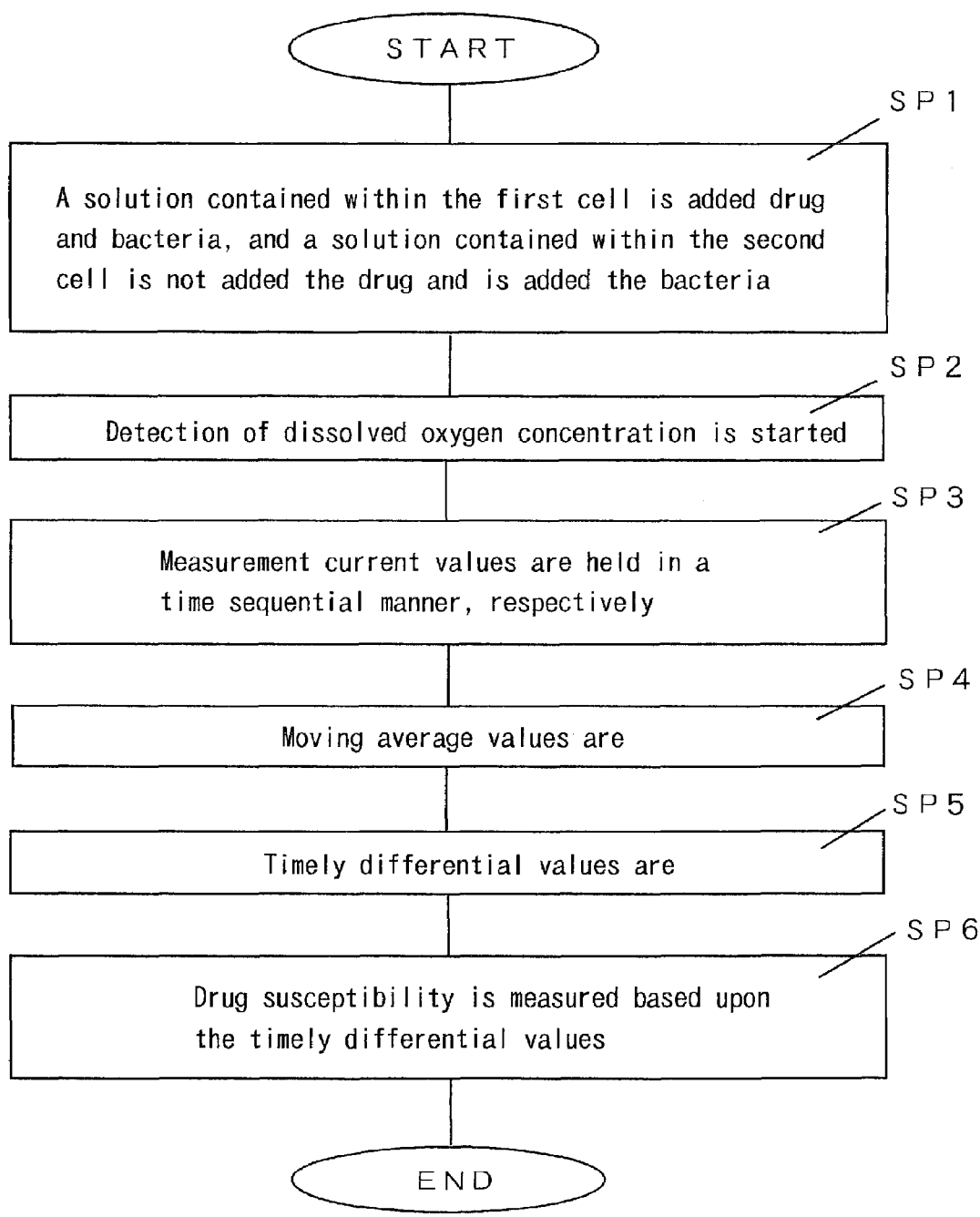
FIG. 2 is a flowchart useful in understanding a drug susceptibility measurement method of an embodiment according to the present invention.

Next, referring to a flowchart illustrated in FIG. 2, operation and effect of the drug susceptibility measurement apparatus of FIG. 1 is described.

In step SP1, drug and bacteria are added to a solution contained within the first cell 1, and bacteria but not drug are added to a solution contained within the second cell 2. In step SP2, detection of dissolved oxygen concentrations by the first oxygen sensor 1a and by the second oxygen sensor 2a, is started. In step SP3, measurement current values output from the first oxygen sensor 1a and the second oxygen sensor 2a are held in a time sequential manner, respectively. In step SP4, moving average values are calculated from the measurement current values respectively held in a time sequential manner. In step SP5, timely differential values are calculated from the pair of the respectively calculated moving average values, by the least squares approximation. In step SP6, drug sensitivity is measured based upon the respectively calculated timely differential values. Then, the series of operations is finished.

Figure 3:
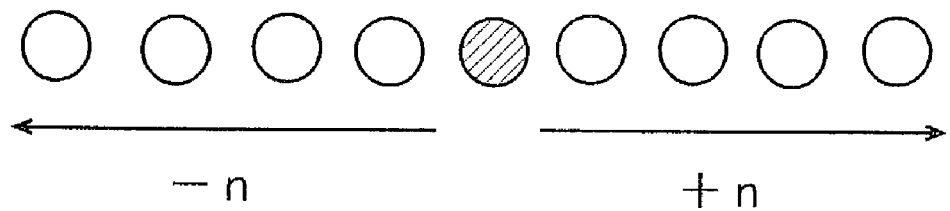
FIG. 3 is a schematic diagram useful in understanding calculation of a moving average value.

Calculation of the moving average value is performed by calculating an average value of the corresponding measurement current value (refer to a circle which is applied hatching), n measurement current values (n is an integer equal to or greater than 1, and is preferable to be selected to have a value of about 5 through 10) prior to the corresponding measurement current value, and n measurement current values following to the corresponding measurement current value, as illustrated in FIG. 3, and by assigning the calculated average value to be the moving average value of the corresponding measurement current value. When the moving average value is calculated in such manner, disturbance due to noise in the moving average value is greatly reduced even when one measurement current value is greatly affected by noise.

Therefore, in the drug susceptibility measurement, improvement in measurement accuracy and shortening of required time period can be achieved.

Drug susceptibility measurement results are represented in Tables 1 and 2. The drug susceptibility measurement results are obtained by employing *S. epidermidis* (Staphilococcus epidermidis), *E. feacalis* (Genus *Enterococcus*) as bacteria, and by determining an amount of bacteria to be 106 cfu/ml. And, PCG (Penicillin G), IPM (Imipenem), MINO (Minocycline), EM (Erythromycin), OFLX (Ofloxacin), ST (Sulfamethoxazole Trimethoprim), VCM (Vancomycin), CMZ (Sefinethazol) are employed as drug. Further, numeric values in column (a) represent MIC values (minimum inhibitory interfering concentration) (g g/ml) (the necessary time is 18 hours) obtained by a conventional measurement method, numeric values in column (b) represent MIC values (g g/ml)/necessary time (minutes) obtained by a measurement method which obtains inclination by a least squares approximation without obtaining moving average value, and numeric values in column (c) represent MIC values (g g/ml)/necessary time (minutes) obtained by a measurement method which obtains a moving average value and then obtains inclination by least squares approximation.

TABLE 1

| Abbreviation | (a) | (b) | w |
|---|---|---|---|
| PCG | 0.06 | 0.12/160 | 0.12/135 |
| IPM | ≦1 | 0.5/160 | 0.5/60 |
| MINO | ≦0.12 | 0.0025/102 | 0.0025/53 |
| EM | ≦0.12 | 0.03/91 | 0.01/50 |
| OFLX | ≦1 | 0.25/98 | 0.12/90 |
| ST | ≦0.25 | 0.5,1/45 | 0.5/37 |
| VCM | ≦1 | 0.25/102 | 0.06/70 |

TABLE 2

| Abbreviation | (a) | (b) | (c) |
|---|---|---|---|
| CMZ | >64 | 256/33 | 512/18 |
| MINO | 1 | 0.1/29 | 0.06/15 |
| EM | 1 | 0.1/46 | 0.06/30 |
| OFLX | 24 | 5/54 | 2/35 |
| VCM | 2 | 1/46 | 0.5/25 |

When the measurement values and necessary times for each method are compared in Tables 1 and 2, it is understood that improvement in measurement accuracy and shortening of required time period can be had, by measuring with the method which obtains a moving average value and then obtains inclination by least squares approximation.

When drug susceptibility was measured by using standard strain 7 bacteria species (*E. coli: colibacillus, K. pneumoniae: Klebsiella pneumoniae, P. aeruginosa: Pseudonomas aeruginosa, P. mirabilis: Proteus mirabilis, S. aureus: Staphylococcus aureus, S. epidermidis: Staphylococcus epidermidis, E. faecalis: Entherococcus faecalis*) and antibiotic 16 drug (CPZ: Cefoperazone, MIND: Minocycline, OFLX: Ofloxacin, ABPC: Ampicillin, LMOX: Latamoxef, PIPC: Piperacillin, GM: Gentamicin, FOM: Fosfomycin, PCG: Penicillin G, EM: Erythromycin, ST: Sulfamethoxazole Trimethoprim, VCM: Vancomycin, IPM: Imipenem, CMZ: Cefinetazole, AZT: Aztreonam, CFS: Cefusulodin), and by determining the bacteria amount to be $10^6$ cfu/ml, a concordance rate to the conventional method was 76% in a case that the measurement was made by a method which obtains inclination by least squares approximation without obtaining a moving average value, while a concordance rate to the conventional method was 91% in a case that the measurement was made by a method which obtains a moving average value and then obtains inclination by least squares approximation.

The present invention has characteristic operation and effect such that disturbance due to noises is reduced so that measurement accuracy is improved in comparison to a case in which a data row is created by simply averaging, and that a required time period can be shortened because continuous analysis is carried out, as a result, improvement in measurement accuracy and shortening of required time period can be had.

What is claimed is:

1. A method of measuring drug susceptibility by detecting, with at least two oxygen electrodes, dissolved oxygen concentration within:
   i) a first solution comprising a target bacteria and a drug; and
   ii) a second solution comprising the target bacteria but not the drug in step i), said method comprising:
      a) collecting multiple output signals from each oxygen electrode at an initial time, and thereafter at predetermined time intervals;
      b) averaging each output signal from each oxygen electrode using a signal value of previous and later output signals to obtain averaged output signals;
      c) calculating a time differential value of each averaged output signal; and
      d) measuring drug susceptibility using the time differential values.

2. A drug susceptibility measurement apparatus that measures drug susceptibility by detecting, with at least two oxygen electrodes, dissolved oxygen concentration within:
   i) a first solution comprising a target bacteria and a drug; and
   ii) a second solution comprising the target bacteria but not the drug in step i), said apparatus comprising:
      a) collecting means for collecting output signals from each oxygen electrode at an initial time, and thereafter at predetermined time intervals;
      b) averaging means for averaging each output signal collected from each oxygen electrode using a signal value of previous and later output signals to obtain averaged output signals;
      c) time differential value calculating means for calculating a time differential value for each averaged output signal; and
      d) drug susceptibility measuring means for measuring drug susceptibility using the calculated time differential values.

* * * * *